(12) United States Patent
Anderson et al.

(10) Patent No.: US 8,357,095 B2
(45) Date of Patent: Jan. 22, 2013

(54) NON-INVASIVE TREATMENT OF FASCIA

(75) Inventors: Richard Rox Anderson, Boston, MA (US); Kirby Vosburgh, Newton, MA (US); John A. Parrish, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 834 days.

(21) Appl. No.: 12/089,643

(22) PCT Filed: Oct. 18, 2006

(86) PCT No.: PCT/US2006/040641
§ 371 (c)(1),
(2), (4) Date: Jul. 14, 2008

(87) PCT Pub. No.: WO2007/047726
PCT Pub. Date: Apr. 26, 2007

(65) Prior Publication Data
US 2008/0269608 A1 Oct. 30, 2008

Related U.S. Application Data

(60) Provisional application No. 60/728,700, filed on Oct. 20, 2005.

(51) Int. Cl.
*A61B 8/00* (2006.01)
(52) U.S. Cl. ........ 600/441; 600/437; 600/439; 606/105; 606/113
(58) Field of Classification Search ................... 600/439, 600/437, 441; 606/105, 113, 41, 28, 46, 606/11
See application file for complete search history.

(56) References Cited

U.S. PATENT DOCUMENTS

| 5,558,092 | A | 9/1996 | Unger et al. | |
|---|---|---|---|---|
| 5,827,204 | A | 10/1998 | Grandia et al. | |
| 6,206,843 | B1 | 3/2001 | Iger et al. | |
| 6,309,352 | B1 | 10/2001 | Oraevsky et al. | |
| 6,309,355 | B1 | 10/2001 | Cain et al. | |
| 6,390,995 | B1 * | 5/2002 | Ogden et al. | 601/2 |
| 6,413,216 | B1 | 7/2002 | Cain et al. | |
| 6,428,532 | B1 | 8/2002 | Doukas et al. | |
| 6,508,774 | B1 | 1/2003 | Acker et al. | |
| 6,524,251 | B2 | 2/2003 | Rabiner et al. | |
| 6,589,174 | B1 | 7/2003 | Chopra et al. | |
| 6,607,498 | B2 | 8/2003 | Eshel et al. | |
| 7,189,209 | B1 * | 3/2007 | Ogden et al. | 601/2 |
| 7,615,016 | B2 * | 11/2009 | Barthe et al. | 601/3 |

(Continued)

OTHER PUBLICATIONS

Bergstein, J.M., "Extremity Compartment Syndrome," in Current Surgical Therapy. 7th ed., Cameron, J, ed. Philadelphia, PA; Mosby; 2001, pp. 1140-1144.

(Continued)

*Primary Examiner* — Brian Casler
*Assistant Examiner* — Joel Lamprecht
(74) *Attorney, Agent, or Firm* — Nutter McClennen & Fish LLP

(57) ABSTRACT

Various methods and devices for minimally invasive treatment and prevention of conditions of the fascia are provided. In one aspect, a method includes providing an acoustic wave source effective to deliver a focused acoustic wave to a target site within a patient's body focusing an acoustic wave through a patient's skin such that at least one location in the patient's fascia is fenestrated in a desired pattern.

27 Claims, 7 Drawing Sheets

U.S. PATENT DOCUMENTS

| | | |
|---|---|---|
| 7,674,233 B2 | 3/2010 | Young et al. |
| 2002/0040199 A1 | 4/2002 | Klopotek |
| 2002/0082528 A1 | 6/2002 | Friedman et al. |
| 2003/0018255 A1 | 1/2003 | Martin et al. |
| 2003/0229283 A1 | 12/2003 | Craig et al. |
| 2004/0162507 A1 | 8/2004 | Govari |
| 2004/0186397 A1* | 9/2004 | Haumann .................. 601/4 |
| 2005/0288680 A1* | 12/2005 | Ingle et al. ................ 606/99 |
| 2006/0074314 A1 | 4/2006 | Slayton et al. |

OTHER PUBLICATIONS

Buchanan et al., "Design and Experimental Evaluation of an Intracavitary Ultrasound Phased Array System for Hyperthermia," IEEE Trasactions on Biomedical Engineering, vol. 41, No. 12, Dec. 1994, pp. 1178-1187.

Daum, et al., "In Vivo Demonstration of Noninvasive Thermal Surgery of the Liver and Kidney Using an Ulatrasonic Phased Array," Ultrasound in Medicine and Biology, vol. 25, No. 7, Sep. 1999, pp. 1087-1098.

Ellsmere et al., "A New Visualization Technique for Laparoscopic Ultrasonography," Surgery, vol. 136, No. 1, Jul. 2004, pp. 84-92.

International Search Report for International Application No. PCT/US06/40641, May 23, 2007; 3 pages.

* cited by examiner

NON-INVASIVE TREATMENT OF FASCIA

FEDERALLY SPONSORED RESEARCH

The invention was made with government support under Grant No. DAMD17-02-2-0006 awarded by the U.S. Department of the Army. The Government has certain rights in this invention.

FIELD OF THE INVENTION

The present invention relates to surgical devices and methods, and in particular to devices and methods for minimally invasive and/or non-invasive treatment and prevention of conditions related to the fascia.

BACKGROUND OF THE INVENTION

The muscle groups in the arms and legs are separated from each other by thick layers of tissue called fascia. Inside each layer of fascia is a confined space, called a compartment, that includes the muscle tissue, nerves, and blood vessels.

Following trauma to the arm and leg muscles, the fascia, unlike other body tissues, are unable to expand. If a compartment swells and the pressure within that compartment increases, the muscles, blood vessels, and nerves contained therein can be compressed, creating a condition called compartment syndrome. At the very least, as a result of compartment syndrome, a patient can experience pain. However, if the pressure in the compartment is high enough, blood flow to the compartment will be blocked, causing permanent injury to the muscle and nerves.

Current treatments for compartment syndrome and other fascial conditions include a fasciotomy, which involves surgically opening the skin, superficial fascia, fat, and overlying muscle to gain access to the deep fascia that confines the compartment. Once access is gained to the deep fascia, the deep fascia is cut to create an opening wide enough to relieve the pressure within the compartment and restore blood flow. This opening is generally left open, and is closed 48 to 72 hours later during a second surgery.

While effective, a fasciotomy is quite invasive, and it creates another wound in tissue that is already injured. Moreover, the fasciotomy requires a sterile environment and time for the blood flow to restore, both of which may not always be available.

Accordingly, there remains a need for improved surgical devices and methods, and in particular, improved devices and methods for treating and preventing compartment syndrome in tissue enclosed by the fascia.

SUMMARY OF THE INVENTION

The present invention provides various methods and systems for minimally invasive and/or non-invasive treatment and prevention of conditions caused by the lack of expansion of the fascia. In fact, the fascia can be treated without creating a surgical opening in the patient's skin. In one aspect, a method includes providing an acoustic wave source effective to deliver a focused acoustic wave to a target site within a patient's body, and focusing an acoustic wave through a patient's skin such that at least one location in the patient's fascia is fenestrated in a desired pattern. In one embodiment, a medium can be applied to the patient's skin adjacent to the target site to allow for propagation of the acoustic waves therethrough. The acoustic waves fenestrate the patient's fascia at a desired location. In another embodiment, the tissue adjacent to the target site can be heated to a temperature such that the tissue is not destroyed. Moreover, the method can include real time imaging the fascia using an imaging source, such as an ultrasound source, that is integrated with the acoustic wave source.

In another aspect, a method for non-invasive treatment and prevention of compartment syndrome includes inducing cavitation within a target region via an acoustic treatment source, focusing the acoustic treatment source, and adjusting a frequency of the acoustic treatment source such that the target region is penetrated. In one embodiment, the method further includes real time imaging the target region using an imaging device that is integrated with the acoustic treatment source using, for example, an ultrasound source. Further, the method can include moving the acoustic treatment source such that cuts or a pattern of fenestrations are formed on the target region.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides methods for minimally invasive and non-invasive treatment and prevention of fascial conditions. While the exemplary embodiments are directed towards treatment and prevention of compartment syndrome in the limbs of a patient, one skilled in the art will appreciate that the present invention can be used to treat any tissue that is up to about 1 mm thick, such as abdominal tissue and extremity tissue. The present invention can also be used to treat a variety of other medical conditions, such as injuries from burns and athletic injuries.

In one exemplary embodiment, the method includes providing an acoustic wave source effective to deliver a focused acoustic wave to a target site within a patient's body, and focusing the acoustic wave through a patient's skin such that at least one location in the patient's fascia is fenestrated in a desired pattern. The method can further include real time imaging of the fascia prior to the application of the acoustic wave in order to determine the location of the target site, during the application of the acoustic wave in order to effect the desired fenestration pattern, as well as after the desired fenestration pattern has been effected to ensure reperfusion of the fascia.

In order to effectively fenestrate the tissue, the acoustic waves can have a low frequency, a high power, and a short pulse. In particular, an exemplary frequency range should be able to penetrate at least 5 cm of soft tissue, and more preferably at least 2 cm of soft tissue. Exemplary frequencies can be in the range of about 0.01 MHz to 5 MHz, and more preferably about 1 MHz. The peak power of the acoustic treatment should be sufficient to denature tissue. Thus, exemplary peak powers are in the range of about 1 W to 1,000 W, more preferably in the range of about 10 W to 100 W, and most preferably in the range of about 10 W to 20 W. The duration of the acoustic treatment can have a length that is effective to cut the fascial tissue without causing unnecessary damage to the target site, as well as the surrounding area, and in an exemplary embodiment the treatment duration is less than 1 second, and more preferably about 1 millisecond.

Figure 1:
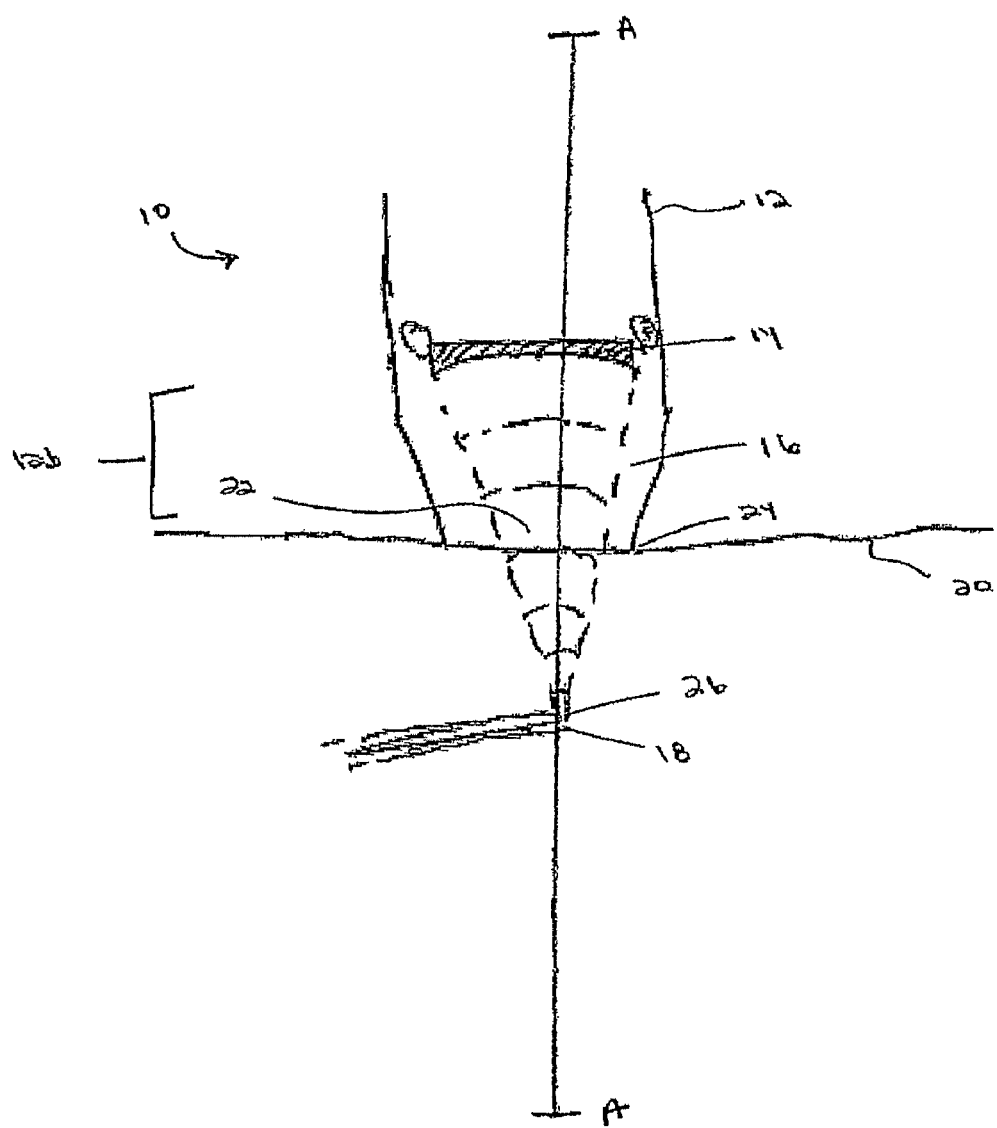
FIG. 1 is a schematic of one exemplary embodiment of a system for use with the methods disclosed herein having a transducer.

The energy source used to deliver the acoustic waves to the patient can have a variety of configurations, however it should be adapted to induce cavitation in tissue with minimal heating of the area surrounding the target site. FIGS. 1-5 illustrate exemplary embodiments of acoustic energy sources that can be used to effect the methods disclosed herein. For example, as shown in FIG. 1, the exemplary wave source 10 includes a housing 12 having a transducer 14 that receives energy from an energy source (not shown) in order to deliver the acoustic waves to a target site 18, i.e., the fascia When delivered, the acoustic waves flow through an offset region 16 located between the transducer 14 and/or a medium 24 placed on the patient's skin 20 and into the target site 18. Moreover, the wave source 10 can optionally include an imaging source (not shown), such as an ultrasound imaging apparatus.

While the wave source can have any configuration that allows it to effectively fenestrate the tissue, in an exemplary embodiment it can be sized such that it can be easily maneuvered and transported. Thus, an exemplary wave source is in the shape of a hand-held wand that can be passed over the target site. Such a device can be sized for convenient one-handed manipulation by a user, For example, the device can have a length in the range of about 1 inch to 4 inch and a width in the range of about ½ inch to 5 inch. The acoustic waves can be produced by a variety of methods as known in the art, such as a single-element transducer or a phased array transducer. In an exemplary embodiment, shown in FIGS. 1-2, a single element transducer can be used. While the transducers can have a variety of configurations, exemplary single-element transducers are similar to those known in the art. Embodiments that incorporate phased array transducers will be discussed in more detail below.

The device can also have a variety of features to protect the skin of the patient from acoustic wave damage. Referring still to FIG. 1, an offset region 16 can be located distal to the transducer 14. While the offset region 16 can have a variety of configurations, in an exemplary embodiment it is a fluid reservoir that is filled with a variety of fluids, such as water or saline, or a gel. The offset region 16 prevents fenestration of the skin and creates a closed surgical site, thereby reducing the trauma and the risk of infection to the surgical site.

One skilled in the art will appreciate that the offset region can vary in size depending upon the type of tissue to be fenestrated. In an exemplary embodiment, the offset region can be in the range of about 1 inch to 8 inches, and more preferably in the range of about 3 inches to 6 inches. Moreover, the offset region can have a fixed or an adjustable size. In an exemplary embodiment, the size of the offset region is adjustable to allow for the wave source to be used with various patients, as well as on various parts of the body. While the size of the offset region can be adjusted in a variety of ways, in one embodiment the offset region can be retractible within the walls of the housing. Alternatively, the transducer can be moveable within the housing, thereby affecting the size of the offset region.

As noted above, the wave source can be adapted to focus the waves onto a target site. In particular, as shown in FIG. 1, the distal end 12b of the housing 12 can be configured to form a focal region 22. This causes the waves to form a focal spot 26, and allows for a more efficient and accurate delivery of energy to the target site 18. While the focal region 22 can be formed in a variety of ways, in an exemplary embodiment, the distal end of the housing 12b can be flexed or telescoping. As shown, the distal end of the housing 12b is telescoping such that it angles inward with respect to the central longitudinal axis A of the wave source 10. One skilled in the art will appreciate that the distal end of the housing can have a variety of geometries, and that the geometry of the distal end of the housing can determine the location of the focal point.

The resulting focal spot can be sized to prevent injury to tissues (not shown) overlying the fascia, as well as to prevent unwanted injury to the muscle tissue (not shown) underlying the target fascia. This can be achieved with about f/1 through f/4 focusing. Thus, in an exemplary embodiment the focal spot can be in the range of about 1 mm to 2 mm. For example, where the source is 1 MHz, the focal spot can be as small as about 1 mm laterally, and about 2 mm along the axis of propagation. This is particularly advantageous in that it is compatible with the thickness of the muscle fascia, which is in the range of about 0.3 mm to 3 mm thick, and more preferably about 1 mm thick.

Figure 2:
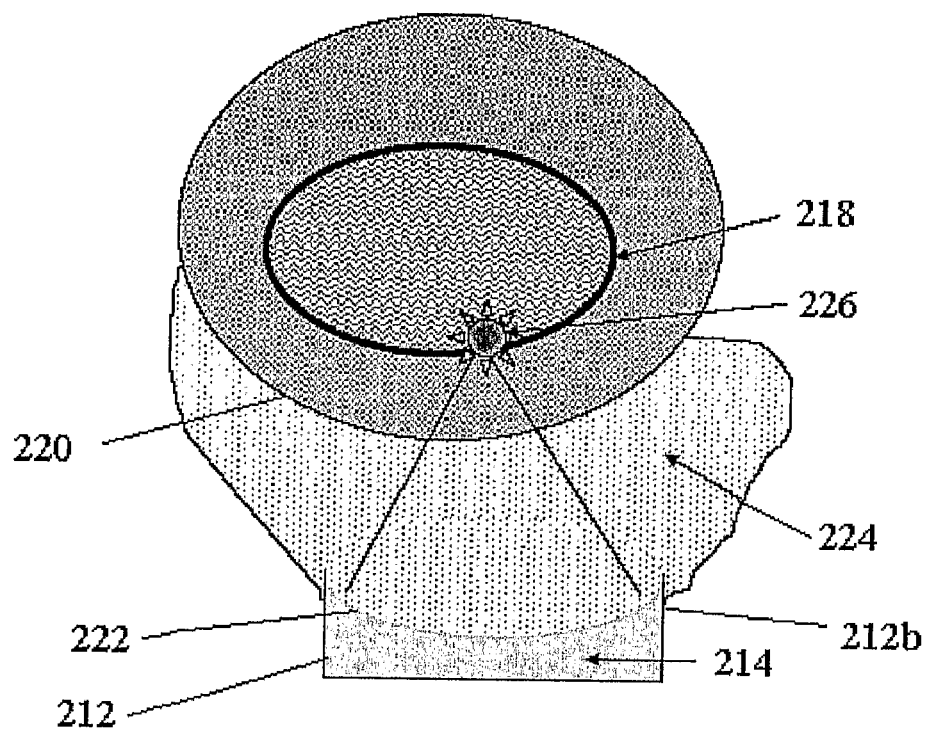
FIG. 2 is a schematic of another exemplary embodiment of a system for use with the methods disclosed herein having a transducer.

FIG. 2 illustrates another wave source that, similar to the wave source in FIG. 1, includes a housing 212 having a single-element transducer 214 to deliver acoustic waves to a target site 218. In particular, the energy flows through a medium 224 placed on the patient's skin and into the target site 218. Instead of the housing having a flex or telescoping distal end to facilitate energy delivery, the distal end of the housing 212b can be configured to form a substantially concave focal region 222 to facilitate formation of the focal point 226, and hence energy delivery to the target site 218. Further, while the wave source shown in FIG. 2 does not have an offset region, one skilled in the art will appreciate that one could be incorporated therein.

Figure 3:
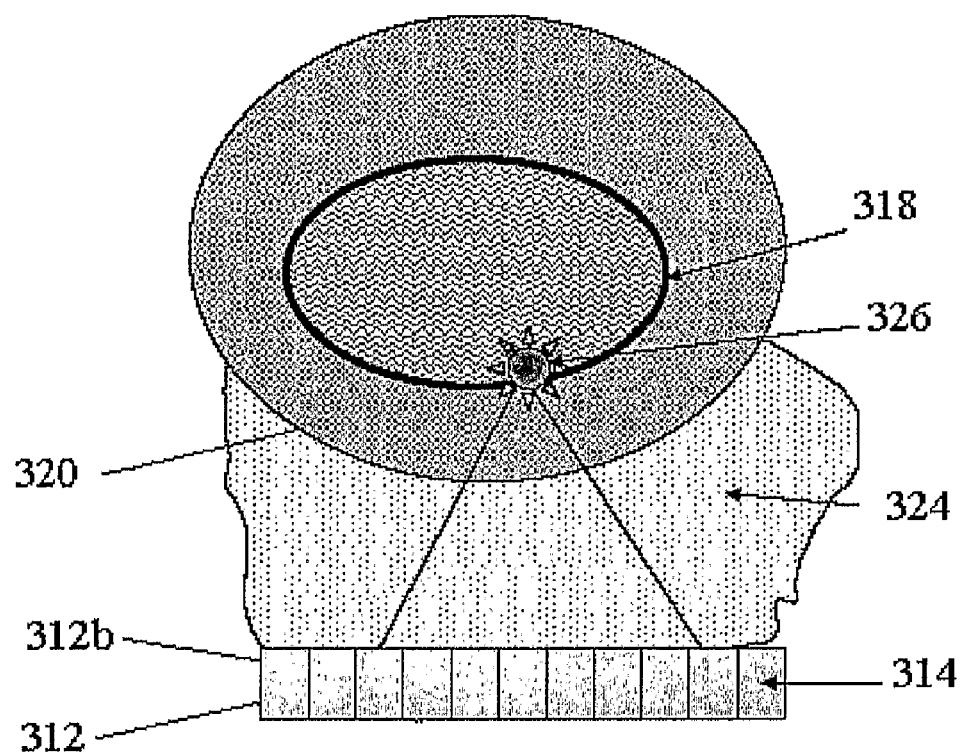
FIG. 3 is a schematic of another exemplary embodiment of a system for use with the methods disclosed herein having a phased array transducer.

As noted above, the transducer can also be a phased array transducer and FIG. 3 illustrates another embodiment of a wave source that, instead of having a single-element transducer, has a phased array transducer. In particular, as shown, the wave source includes a housing 312 having the transducer 314 located therein. In use, as will be discussed in more detail below, a medium 324 is placed between the patient's skin and the distal end of the housing 312b to facilitate contact therebetween and facilitate energy delivery to the focal point 326 and target site 318. The transducers can have a variety of configurations, and exemplary phased array transducers are similar to those discussed in Daum et al., "In vivo demonstration of noninvasive thermal surgery of the liver and kidney using an ultrasonic phased array," *Ultrasound in Medicine & Biology,* 25(7):1087-98 (September 1999) and Buchanan et al., "Design and experimental evaluation of an intracavitary ultrasound phased array system for hyperthermia," *IEEE Transactions on Biomedical Engineering,* 41(12):1178-87 (December 1994), both of which are herein incorporated by reference. While both single-element transducers and phased array transducers are effective to provide energy delivery to the target site, a person skilled in the art will appreciate that the phased array transducer is particularly advantageous because the electrical beam controlling or beam forming mechanism in a phased array transducer provides rapid and flexible focusing and steering, as well as an adjustable aperture to sequentially and confocally address a large area of interest without mechanical movement.

The wave source, such as any of the exemplary wave sources shown in FIGS. 1-3, can also optionally include an imaging device that allows a user to perform the fasciotomy while imaging in real time to effectively aim the treatment to the target fascia, and to verify that the pressure has been released. While any device known in the art can be used to image the fascial compartment, in an exemplary embodiment an ultrasound device, as is known in the art, is used. This is particularly advantageous in that it provides for real time monitoring of the muscle site. Furthermore, the ultrasound imaging apparatus can be equipped with Doppler frequency detection as a means for verifying blood flow back into the compartment once tissue fenestration has occurred.

Figure 4:
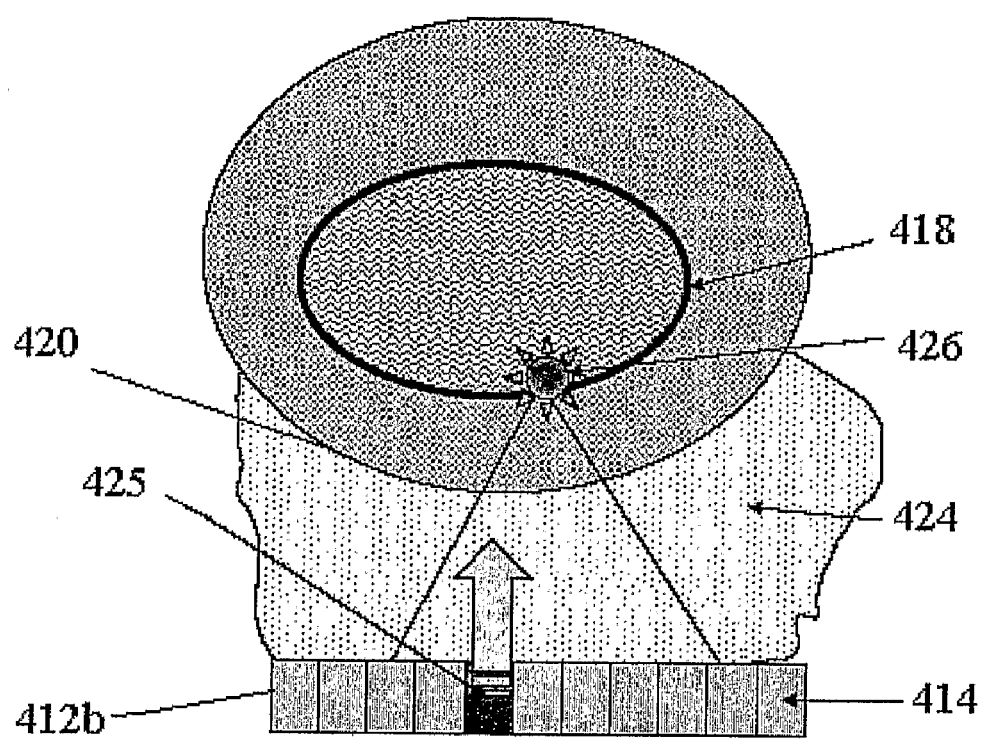
FIG. 4 is a schematic of yet another exemplary embodiment of a system for use with the methods disclosed herein having an imaging component combined with the energy delivery component.
Figure 5:
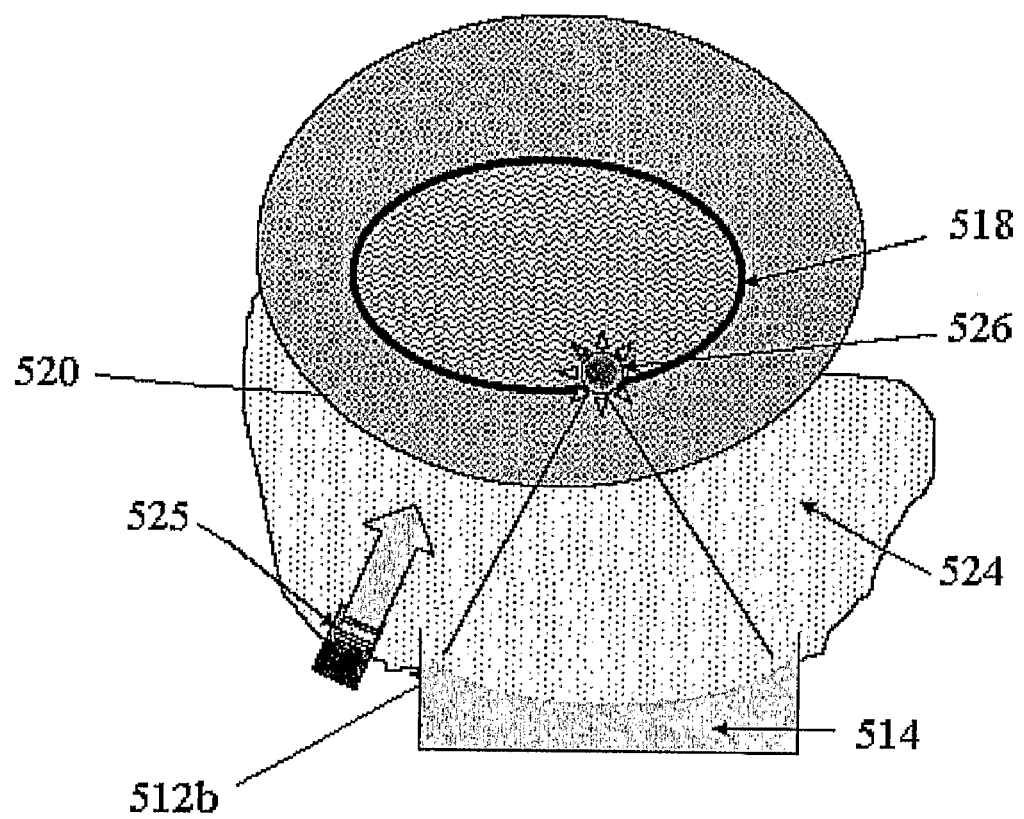
FIG. 5 is a schematic of another exemplary embodiment of a system for use with the methods disclosed herein having an imaging component that is separate from the energy delivery component.

A person skilled in the art will appreciate that the imaging device can be formed integral with the wave source or separate therefrom. For example, FIG. 4 illustrates one embodiment of a wave source that includes an imaging device 425 formed integrally with the transducer 414 to facilitate the delivery of energy to the focal point 426 and hence the target site 418. Similar to FIG. 4, FIG. 5 also illustrates a wave source having a transducer 514 and an imaging device 525 to facilitate energy delivery to the focal point 526 and the target site 518, however the imaging device 525 is formed separate from the transducer 514. While both embodiments are effective to facilitate energy delivery, an imaging device that is integrated with the wave source is particularly advantageous in that it prevents misalignment of the transducer and the imaging device.

An exemplary method can use any of the wave source devices described above. While imaging can take place at any point throughout the procedure, in an exemplary embodiment, the affected area is imaged prior to the delivery of any acoustic energy in order to determine the location of the fascia, i.e., the target site. Once the target site is determined, the physician should apply a medium to the surface of the tissue to help ensure that the wave source makes a secure contact with the patient's skin. Moreover, since such waves cannot penetrate air, the medium helps eliminate air pockets between the device and the skin.

One skilled in the art will appreciate that the medium can have a variety of configurations, however in an exemplary embodiment, and referring back to FIG. 1, the medium can be a flexible membrane 24 that is located at the distal most end of the offset region 16 such that it rests on the patient's skin 20. Alternatively, as shown in FIGS. 2-5, the flexible membrane 224, 324, 424, 524 is an element that is separate from the offset region and can be positioned between the distal end of the housing 212b, 312b, 412b, 512b and the patient's skin 220, 320, 420, 520. While the flexible membrane can be made of any biocompatible material, in an exemplary embodiment, it can be made of silicone rubber or Mylar, and the membrane is particularly advantageous in that it prevents the transducer from clogging. Alternatively, the medium can include a flexible membrane as well as a liquid or a gel that is applied to the patient's skin, as is known in the art.

Following application of the medium, if necessary, and while still maintaining an image of the target site to insure accuracy of the fenestrations, the physician can selectively deliver the acoustic energy to relieve the pressure of the fascia. To be effective, a fasciotomy requires more than just creating a hole in the fascia. Thus, the focused acoustic source can be delivered in a variety of configurations, most preferably in an array of fenestrations. One skilled in the art will appreciate that this array of fenestrations can be formed as a result of moving the wave source by hand over the target site and manually selecting the pulses of energy to be delivered, or by using a wave source that has an automated energy delivery.

Figure 6A:
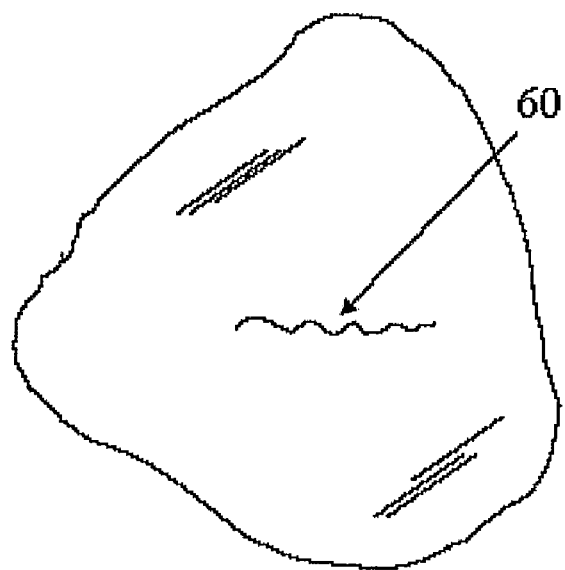
FIGS. 6A-6B are schematics of a substantially linear cut formed by the methods disclosed herein (FIG. 6A) and the cut opening as a result of release of pressure in the compartment (FIG. 6B)
Figure 6B:
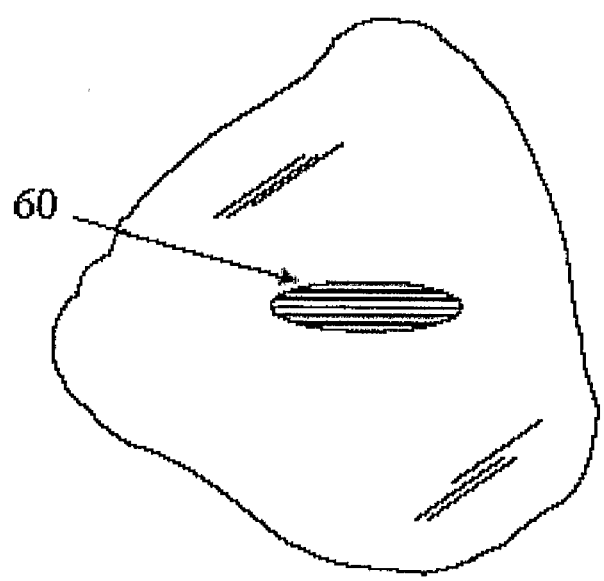

While the array of fenestrations can have any configuration that allows the pressure in the compartment to be released, in one exemplary embodiment, the energy can be delivered such that a substantially linear cut 60 is made in the fascia, as shown in FIG. 6A. This cut 60 is formed as a result small fenestrations, e.g., about 1 cm in length, that are aligned end to end. One skilled in the art will appreciate that a similar methodology can be used if the physician desires to form a curved cut. Once formed, as shown in FIG. 6B, the resulting substantially linear cut 60 will expand due to the release of pressure in the compartment.

Figure 7A:
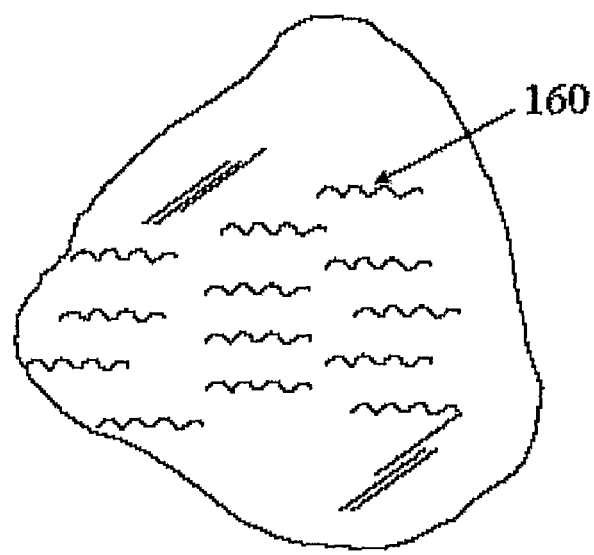
FIGS. 7A-7B are schematics of an array of fenestrations formed by the methods disclosed herein (FIG. 7A) and the fenestrations opening as a result of the release of pressure in the compartment (FIG. 7B).

Alternatively, the energy can be delivered in an array of fenestrations that has a configuration similar to that used in expanded skin grafts or expanded metal sheets. For example, as shown in FIG. 7A, about fifty fenestrations 160 can be formed such that they are staggered with respect to one another. While the fenestrations 160 can have a variety of sizes, each exemplary fenestration is about 1 cm in length.

Figure 7B:
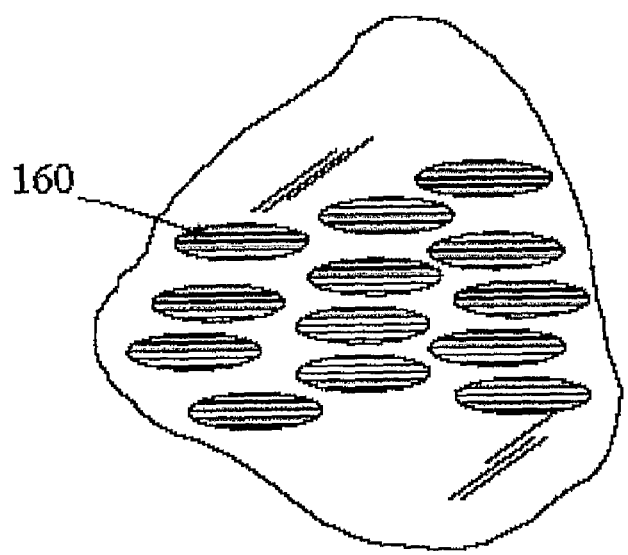

When the pressure in the fascia is released, each fenestration 160 expands thus causing a number of small holes to be formed within the fascia, as shown in FIG. 7B. This is particularly advantageous in that it causes less damage to the compartment than a single, larger cut, while still allows for the release of pressure. Moreover, this configuration promotes faster and better healing of the compartment.

One skilled in the art will appreciate that the methods disclosed herein can have a variety of other configurations to facilitate the treatment and prevention of compartment syndrome. For example, once the desired fenestration pattern has been attained, a physician can use Doppler imaging to insure that the muscle has reperfused, Alternatively, the system can include a tracker that allows the user coordinate where to begin applying the acoustic wave treatment on the tissue. A person skilled in the art will appreciate that the tracker system can use any of a variety of systems to register the ultrasound fenestration pattern with the fascia, and exemplary tracker systems include those as mentioned in Ellsmere et al., "A new visualization technique for laparoscopic ultrasonography," *Surgery,* 136(1):84-92 (July 2004), which is herein incorporated by reference.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A method for non-invasive treatment and prevention of fascial conditions, comprising:
    focusing an acoustic wave to a target site of one or more muscles within a patient's body to treat compartment syndrome, the one or more muscles having fascia disposed therearound; and
    applying the acoustic wave to the target site through a patient's skin to fenestrate one or more cuts in a desired pattern in at least one location in the patient's fascia.

2. The method of claim 1, further applying a medium to the patient's skin adjacent to the target site.

3. The method of claim 1, further comprising non-destructible heating of tissue adjacent to the target site.

4. The method of claim 1, further comprising imaging the fascia using an imaging source that is integrated with the acoustic wave source.

5. The method of claim 4, wherein the imaging source is an ultrasound source.

6. The method of claim 1, wherein the acoustic wave is delivered to the target site at a frequency in the range of about 0.5 MHz to about 5 MHz.

7. The method of claim 1, wherein the acoustic wave is delivered to the target site at a frequency in the range of about 1 MHz.

8. The method of claim 1, wherein the acoustic wave source is focused to form a focal spot in the range of about 0.3 mm to about 3.0 mm.

9. The method of claim 1, further comprising adjusting a peak power of the acoustic source in the range of about 10 W to about 100 W prior to fenestration of the fascia.

10. The method of claim 1, wherein the frequency of the acoustic wave source is adjusted to the range of about 10 W to about 20 W prior to fenestration of the fascia.

11. A method for non-invasive treatment and prevention of compartment syndrome, comprising:
    inducing cavitation into a target region of one or more muscles within a patient's body, the one or more muscles having fascia disposed therearound, thus forming one or more cuts in the fascia using an acoustic treatment source to treat compartment syndrome
    focusing the acoustic treatment source; and
    adjusting a frequency of the acoustic treatment source such that the fascia is penetrated.

12. The method of claim 11, further comprising imaging the target region using an imaging device that is integrated with the acoustic treatment source.

13. The method of claim 12, wherein the imaging device is an ultrasound source.

14. The method of claim 11, further comprising moving the acoustic treatment source such that cuts or a pattern of fenestrations are formed on the target region.

15. The method of claim 11, wherein the step of inducing cavitation further includes generating acoustic waves in the range of about 0.5 MHz to about 5 MHz.

16. The method of claim 11, wherein the step of inducing cavitation further includes generating acoustic waves in the range of about 1 MHz.

17. The method of claim 11, wherein the treatment source is focused to form a focal spot on the target region in the range of about 0.3 mm to about 3.0 mm.

18. The method of claim 11, wherein the frequency a peak power of the treatment source is adjusted to the range of about 10 W to about 100 W.

19. The method of claim 11, wherein the frequency a peak power of the treatment source is adjusted to the range of about 10 W to about 20 W.

20. The method of claim 1, wherein the one or more cuts is an array of fenestrations.

21. The method of claim 1, wherein the one or more cuts is one or more substantially linear cuts.

22. The method of claim 1, wherein the one or more cuts is one or more curved cuts.

23. The method of claim 1, wherein the one or more cuts is a plurality of cuts and the plurality of cuts are staggered with respect to one another.

24. The method of claim 1, wherein the one or more cuts is an array of fenestrations.

25. The method of claim 1, wherein the one or more cuts is one or more substantially linear cuts.

26. The method of claim 1, wherein the one or more cuts is one or more curved cuts.

27. The method of claim 11, wherein the one or more cuts is a plurality of cuts and the plurality of cuts are staggered with respect to one another.

* * * * *